United States Patent [19]

Kosova

[11] Patent Number: 4,827,916

[45] Date of Patent: May 9, 1989

[54] VENT FOR USE IN AN ORTHOPEDIC CAST

[76] Inventor: Ghenz Kosova, 647 SW 17th Court, Boca Raton, Fla. 33432

[21] Appl. No.: 75,558

[22] Filed: Jul. 20, 1987

[51] Int. Cl.$^4$ ............................................. A61F 15/00
[52] U.S. Cl. ................... 128/91 R; 128/91 A
[58] Field of Search .............. 128/91 R, 91 A, 90, 128/89, 87, 83; 236/49, 98.40.18, 98.1, 98.05

[56] References Cited

U.S. PATENT DOCUMENTS

| | | | |
|---|---|---|---|
| 2,273,792 | 2/1942 | Brown | 128/91 A |
| 2,704,067 | 3/1955 | Moses | 128/90 |
| 2,731,963 | 1/1956 | Blank | 128/91 A |
| 2,822,806 | 2/1958 | Blank | 128/91 A |
| 2,837,088 | 6/1958 | Moses | 128/91 A |
| 3,116,731 | 1/1964 | Baxter | 128/91 R |
| 3,307,537 | 3/1967 | Simon et al. | 128/90 |
| 3,656,477 | 4/1972 | Thomas et al. | 128/91 R |
| 3,762,406 | 10/1973 | Wells | 128/91 R |
| 3,998,220 | 12/1976 | Cleer Jr. et al. | 128/91 R |
| 4,174,716 | 11/1979 | Treace | 604/204 |
| 4,387,710 | 6/1983 | Beatty III | 128/91 R |

Primary Examiner—Robert A. Hafer
Assistant Examiner—Kevin G. Rooney
Attorney, Agent, or Firm—John H. Faro

[57] ABSTRACT

A vent for use in an orthopedic cast of a prescribed thickness comprises a plastic base tab having a substantially elliptical aperture therein and a wall around the periphery of the aperture that rises from one side of the tab to a height about equal to the prescribed cast thickness. The wall may be bowed inwardly. The novel vent may be available singly, or connected together by their tabs, or connected together with spacers therebetween.

13 Claims, 1 Drawing Sheet

4,827,916

VENT FOR USE IN AN ORTHOPEDIC CAST

BACKGROUND OF THE INVENTION

1. Field of the Invention

This invention relates to ventilated orthopedic casts and particularly to a novel vent for use in such orthopedic casts.

2. Description of the Prior Art

Orthopedic casts are used to immobilize a portion of a person's body. Often, such casts cover substantial portions of the body and must remain in place for weeks and sometimes for months. Such casts are usually prepared in place by winding bandages that are impregnated with plaster or an air-setting plastic material around the part of the body of interest. Without ventilation, these casts are hot and uncomfortable, and do not provide ventilation for removing perspiration or other moisture from inside the cast. Insufficient ventilation enables a bacterial buildup to occur, producing unpleasant odors, skin irritations, itching and other discomforts. In some cases, insufficient ventilation has caused serious deterioration of the skin inside the cast.

U.S. Pat. No. 2,704,067 to E. Q. Moses discloses the use of vents that are positioned in the cast while the impregnated bandage is being wound upon the body part of interest. These vents, which can be positioned singly or in strips containing a plurality of vents, are generally round in shape and rather bulky in design, so that the vent is not very convenient or economical to use. U.S. Pat. Nos. 3,116,731 to T. E. Baxter, 3,307,537 to G. B. Simon et al, 3,656,477 to B. E. Thomas, 3,762,406 to G. M. Wells, and 3,998,220 to C. W. Cleer, Jr. et al disclose alternative round vents for use in orthopedic casts. While each of the prior vents performs to some degree the function of ventilating the cast, they nevertheless are not convenient or economical to use. Also, voids may be left on opposite sides of a round vent when the impregnated bandage is wound on the body part of interest.

OBJECTS OF THE INVENTION

An object of this invention is to provide a novel vent for an orthopedic cast.

Another object is to provide a novel vent that can be positioned in the cast while impregnated bandage is being wound upon the body part.

Still another object is to provide a novel vent that is especially shaped to be wound into the impregnated bandage while the cast is being prepared.

Further objects is to provide a novel vent that is more convenient to use in preparing orthopedic casts than prior vents.

A still further object is to provide a novel vent which enables the cast thickness to be gauged and uniformly set, throughout the area where the vents and vent strips are placed.

A still yet further object is to provide a novel vent that is more economical to use in orthopedic casts that prior vents.

SUMMARY OF THE INVENTION

The novel vent for use in an orthopedic cast of a prescribed thickness comprises a base tab having a substantially elliptical aperture therein and a wall around the periphery of the aperture that rises from one side of the tab to a height about equal to the prescribed thickness of the cast. The tab may vary in shape. The shaape of the elliptical wall around the elliptical aperture permits the adjacent edges of the bandage, as it is wrapped around the body part of interest, to close around the wall without leaving a void. As the cast material hardens the vents are permanently encases, allowing air to pass through the cast.

In a preferred form, the wall of the vent is bowed inwardly to permit expansion of the cast while the impregnant in the layers of bandage is hardening. The novel vent is preferably made of a brittle plastic and can be available singly, or connected together by their tabs, or connected together with spacers having a predetermined dimension therebetween. Where the multiple vents are connected together they can be cracked apart, optionally aided with score marks therebetween. Thus, the novel vent is low in cost and is available in forms that are conveniently and economically used. The casts produced with the novel vent are more comfortable and can be left in place longer than casts without vents.

DETAILED DESCRIPTION OF THE INVENTION INCLUDING THE PREFERRED EMBODIMENTS

Figure 1:
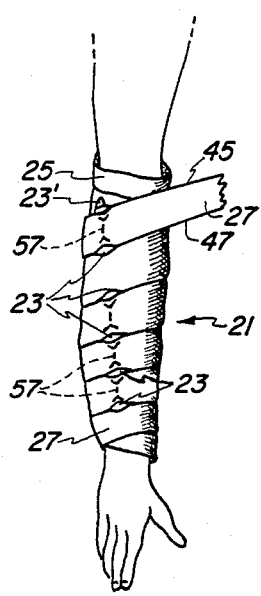
FIG. 1 is an elevational view showing the novel vent being installed in an orthopedic cast on the forearm of a person.

The following description of some of the preferred embodiments of the concepts of this invention is made in reference to the accompanying figures. Where an individual structural element is depicted in more than one figure, it is assigned a common reference numeral for simplification of identification and understanding.

FIG. 1 illustrates a cast (21) including the novel vents (23) in the process of being made on a persons forearm. Except for the novel vents (23), the process is well-known. A lining (25) of soft and porous material, such as a cotton gauze or a woven cotton sleeve is applied to the surface of the skin, principally to prevent abrasion. Then, a bandage (27) impregnated with a suitable material that hardens or sets within a prescribed time interval is wrapped around the forearm over the lining (25). The hardening material may be wet Plaster of Paris or an air-setting polymeric material. In this example, the bandage (27) is about 3 inches wide, although it may be other widths.

The bandage (27) is wound around the forearm so that several layers are applied. After the hardening material has set, the cast (21) comprises a laminate that immobilizes the particular body part, which is a forearm in this example. FIG. 1 shows the first layer of bandage (27) being wound. As this first layer is being wound, the novel vent, shown in detail in FIGS. 2, 3 and 4, is inserted in the winding at desired locations.

The novel vent (23) includes a thin planar base tab (29) having a substantially elliptical aperture (31) therein. The aperture (31) has a major axis (33) and a minor axis (35), and is about ⅝ inch long and about 5/16 inch wide. The aperture (31) at the ends of the major axis (33) may be pointed or rounded. The base tab (29) is about 1/16 inch thick and can be of any convenient thickness, preferably in the range of 1/64 to ⅛ inch. The base tab (29) may be of any shape, such as round, triangular, square; but is preferably substantially elliptical.

Figure 2:
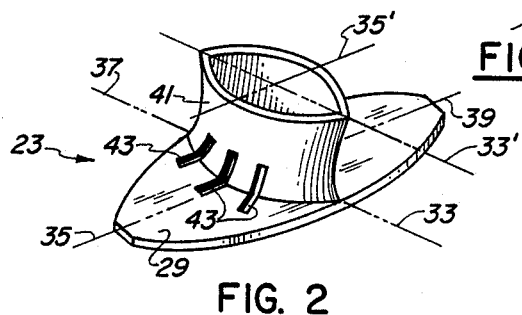
FIG. 2 is a perspective view of a preferred embodiment of the novel vent.
Figure 3:
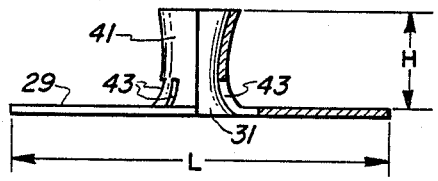
FIGS. 3 and 4 are, respectively, a partially cut away view and a plan view of the novel vent shown in FIG. 2.
Figure 4:
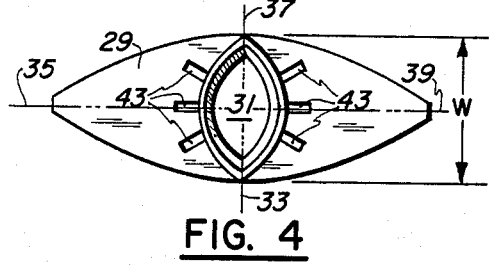

As shown in FIGS. 2 to 4, the base tab (29) is elliptical having a minor axis (37) and a major axis (39), which are coincident with the major axis (33) and the minor axis (35), respectively, of the aperture (31). The tab (29) can have other dimensions and different proportions. The tab (29) of the preferred embodiment has length L of about 1½ inches and a width W of about ¾ inch.

The novel vent (23) also has a wall (41) around the periphery of the aperture (31) that rises from one side of the tab (29) to a height "H" about equal to the desired or prescribed thickness of the cast. The height "H" of the wall (41) in the preferred embodiment is about ⅛ inch, although it can have other heights. The height H of the wall (41) can be used as a gauge for the thickness of the cast (21). The opening at the top of the wall (41) has substantially the same size and shape as the aperture (31) in the base tab (29) with similar major and minor axis (33') and (35'). However, the wall (41) between the bottom and top thereof is bowed inwardly, thereby slightly reducing the opening defined by the wall (41). The bowed wall (41) adds to the strength of the wall, allows for change in size of the cast, and better anchors the vent (23) in the cast (21). The wall (41) may be 1/16 to 1/64 inch thick. The minimum opening occurs about halfway up the bowed wall where its dimensions are about ½ inch along the major axis and about ¼ inch along its minor axis.

The vent (23) also has several slots (43) in the lower part of the wall (41). The slots (43) extend into the adjacent portion of the tab (29). The slots (43) are about 1/16 inch wide and about ⅛ inch long in each of the wall (41) and the tab (29). These slots (43) aid in distributing and collecting ventilating air into and from inside the cast (21).

Referring again to FIG. 1, as the first layer of impregnated bandage (27) is being wound around the body part of interest, one side of the tab (29) is inserted under outer edge (45) the last winding (vent (23'). Then, the next turn of the bandage (27) places the inner edge (47) adjacent the outer edge 45 and over the rest of the tab (29) of the vent (23'). Thus, a multiplicity of the novel vents (23) can be placed in the cast in almost any density and arrangement while the cast is being made.

The novel vent is preferably made of a light brittle plastic material with relatively thin walls. Such a construction is easily made by automatic molding machinery so that the cost and weight of the vents is small compared to the cost and weight of the cast. Also, the time and skill required to position the vents in the cast (21) does not add substantially to the cost of making the cast (21).

After the first layer of bandage (27) has been wound on the body part, successive layers may be wound on top of it with the novel vents falling between successive parts of the outer and inner edges (45) and (47) of the bandage (27). When the desired number of layers of impregnated bandage (27) have been positioned, the end thereof is tied down and the windings permitted to harden or set to form the final ventilated cast (21).

Figure 5:
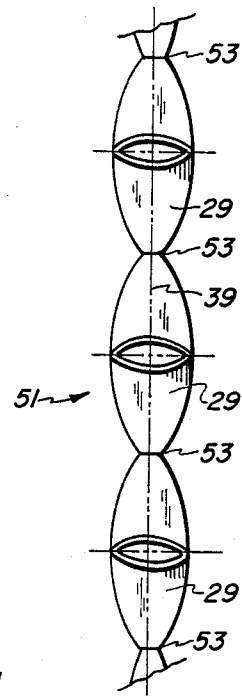
FIG. 5 is one form of a strip comprising a plurality of the novel vents connected directly one to the other in a series.

The novel vent (23) may be provided in separate single units as shown in FIGS. 2 to 4. A multiplicity of such units may also be made available in rolled-up strips (51). As shown in FIG. 5, in such strips (51), the tabs (29) are connected together successively at the ends of the major axes of the tabs (29). The successive tabs (29) may be broken apart manually at the connecting means therebetween where the material is thinnest. Manual separation of the tabs, may be aided by providing a score line or weakening groove (53) at the connecting means.

Figure 6:
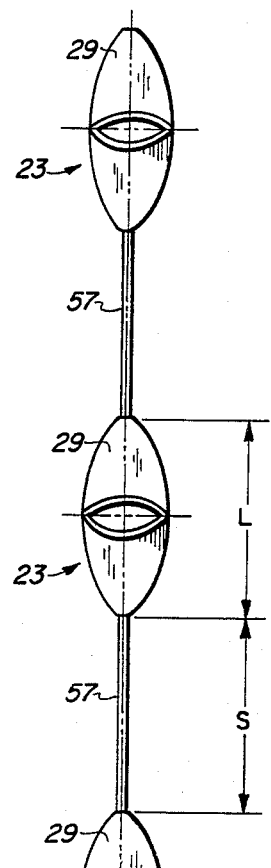
FIG. 6 is another form of strip comprising a plurality of the novel vents connected one to the other in a series with spacers therebetween.
Figure 6:
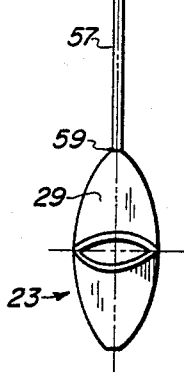

In still another arrangement, several vents are available in straight strips with spacers or bridges of predetermined length therebetween. A preferred straight strip (55) shown in FIG. 6 comprises a single molded plastic strip comprising four units (23). Each pair of vents (23) is separated by a string-like spacer or bridge (57) about 1/16 inch thick and ⅛ inch wide. A vent (23) can be separated from a spacer (57) at the connecting means therebetween by manually fracturing the connecting means. Separation may be aided by a score line or weakening groove (59) at the connecting means. The spacers (57) can be of any lengths, but are preferably of such length that the width of the bandage fits comfortably between the walls of successive vents. As shown in FIG. 1, the bridges (57) are left in place as the bandage (27) is wound. The number of connected vents (23) is determined by breaking off the desired number of vents (23) with the spacers (57) between at the time the cast (21) is being made.

There has been describe a novel orthopedic vent that is especially shaped and otherwise adapted to be wound into an impregnated bandage while an orthopedic cast is being made. The novel vent is more convenient and more economical to use than prior vents. The ventilated casts produced with the novel vents are adequately ventilated so as to avoid the problems encountered with prior casts.

The foregoing figures and descriptions thereof are provided as illustrative of some of the preferred embodiments of the concepts of this invention. While these embodiments represent what is regarded as the best mode for practicing this invention, they are not intended as delineating the scope of the invention, which is set forth in the following claims.

What is claimed is:

1. A vent for use in an orthopedic cast having a prescribed thickness comprising a single base tab having a substantially elliptical aperture therein and an integral elliptical wall around the periphery of said aperture, said wall rising from one side of said base tab to a height about equal to said prescribed thickness, said aperture having a major axis and a minor axis, said wall defining a substantially elliptical opening therethrough, and wherein said wall and said opening are bowed inwardly to a maximum at about half the height of said wall.

2. The vent defined in claim 1 wherein said base tab is elliptical and has a major axis and a minor axis, the major axis of said aperture being substantially coincident with the minor axis of said base tab.

3. The vent defined in claim 1, including means connecting said vent with a substantially identical vent, said connecting means being attached to the base tabs of said vents along extensions of the minor axes of the apertures in said vents, said connecting means being adapted to be broken apart manually.

4. A strip comprising a plurality of the vents defined in claim 3, said vents being connected successively to one another by said connecting means attached to said base tabs.

5. The strip defined in claim 4 comprising four of said vents connected to one another through a spacer of predetermined length.

6. A vent for use in an orthopedic cast having a prescribed thickness and produced by wrapping with a bandage impregnated with a hardenable material, said vent comprising a single substantially elliptical planar base tab having a substantially elliptical aperture therein, the major axis of said aperture being substantially coincident with the minor axis f said tab, and an integral substantially elliptical wall around the entire periphery of said aperture, said wall rising from only one side of said tab to a height about equal to said prescribed thickness, said wall defining a substantially elliptical opening therethrough, and wherein said wall and said opening are bowed inwardly to a maximum at about half the height of said wall, said vent having a plurality of spaced slots therein radiating from the juncture between said base tab and said wall and extending a substantial distance into both said tab and said wall.

7. The vent defined in claim 6 wherein the maximum dimension of said aperture along said major axis of said aperture is slightly less than minimum dimension of said tab along said minor axis of said tab.

8. The vent defined in claim 6 wherein the ratio of the maximum dimension parallel to said major axis of said aperture to the minimum dimension parallel to said minor axis of said aperture of the minimum opening through said wall where said wall is bowed inwardly to a maximum is about 2 to 1.

9. The vent defined in claim 6 including means connecting the base tab of said vent to the base tab of a substantially identical vent, said connecting means being adapted to be broken apart manually.

10. The vent defined in claim 9 wherein said connecting means is attached to said base tabs along extensions that are substantially parallel to said minor axis of said aperture.

11. The vent defined in claim 9 wherein said connecting means is a narrow string-like member connected at each end to one of said tabs.

12. A strip comprising a plurality of vents defined in claim 6, said vents being successively connected to one another through narrow string-like spacer members attached by connecting means to the edges of the base tabs of said vents.

13. The strip defined in claim 12 wherein said spacer members are attached through said connecting means at about the intersection of the major axis of said tab with the edge thereof.

* * * * *